United States Patent [19] [11] Patent Number: 4,574,623
Neumann [45] Date of Patent: Mar. 11, 1986

[54] PROCESS AND APPARATUS FOR MEASURING THE FLOW CHARACTERISTICS OF A FLUSHED PIGMENT

[75] Inventor: John A. Neumann, Winamac, Ind.

[73] Assignee: Sun Chemical Corporation, New York, N.Y.

[21] Appl. No.: 655,415

[22] Filed: Sep. 28, 1984

[51] Int. Cl.$^4$ .............................................. G01N 11/04
[52] U.S. Cl. ........................................................ 73/56
[58] Field of Search ............................................. 73/56

[56] References Cited

U.S. PATENT DOCUMENTS

| 2,780,096 | 2/1957 | Noble et al. | 73/56 X |
| 3,242,720 | 3/1966 | Zavasnik | 73/56 |
| 3,360,986 | 1/1968 | Rothschild | 73/56 |
| 3,625,050 | 12/1971 | Noetzel et al. | 73/56 |
| 3,803,902 | 4/1974 | Rusk | 73/56 |

FOREIGN PATENT DOCUMENTS

| 1265456 | 4/1968 | Fed. Rep. of Germany | 73/56 |
| 21542 | 2/1983 | Japan | 73/56 |
| 169848 | 6/1965 | U.S.S.R. | 73/56 |

Primary Examiner—Stewart J. Levy
Assistant Examiner—Joseph W. Roskos
Attorney, Agent, or Firm—Mitchell Bittman

[57] ABSTRACT

A process and apparatus are described for measuring the flow characteristics of a non-powdered material, e.g., a flushed pigment, and correlating them with actual production practice. The non-powdered material is placed into a cylinder having an orifice at its base, a piston with a known weight is placed on top of the material in the cylinder and after the orifice at the bottom of the cylinder is opened the distance traveled by the piston in a given time is measured and compared to the distance the piston travels with a known standard material.

14 Claims, 1 Drawing Figure

U.S. Patent   Mar. 11, 1986   4,574,623
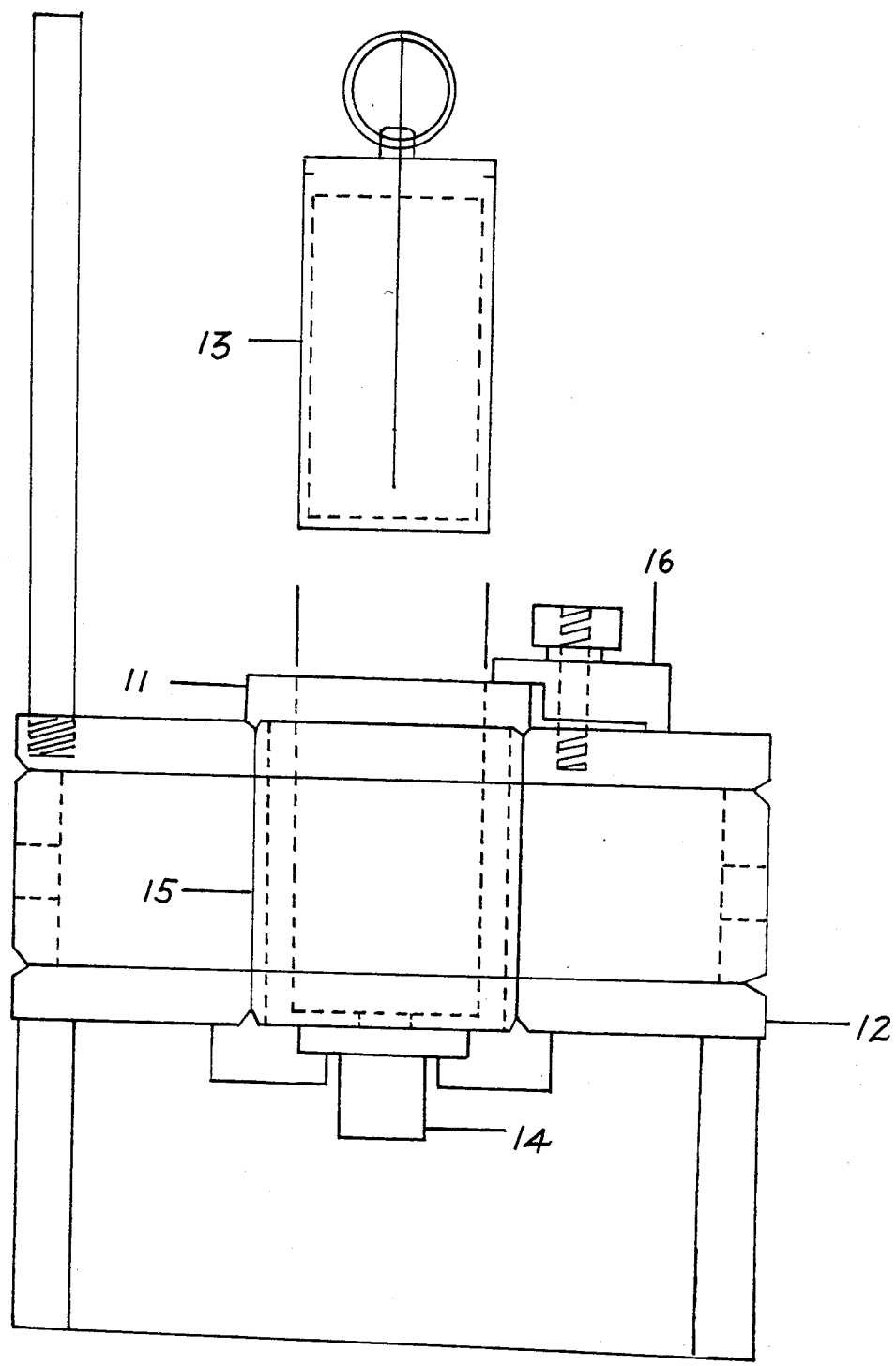

PROCESS AND APPARATUS FOR MEASURING THE FLOW CHARACTERISTICS OF A FLUSHED PIGMENT

This invention relates to the flow characteristics of a non-powdered material. More particularly it relates to a process and apparatus for measuring the flow characteristics of a flushed pigment.

BACKGROUND OF THE INVENTION

Flushed pigments, that is, pigments that have been transferred as pigment particles directly to a non-aqueous phase from the aqueous phase, are widely used in printing inks and paints because they retain their fine particle structure in the flushed form, resulting in products having excellent color strength, brilliance, gloss, and transparency. Furthermore, since they do not contain hard agglomerates, they can be dispersed more readily in the selected vehicle.

In order to produce inks, paints, and the like that have these superior qualities, the flushed pigment must have certain properties, foremost among which is body length/stiffness. If the flushed pigment has too much body length, it may flow easily from the supply bin, but the finished ink may not print well.

If the flushed pigment, hereinafter referred to as "flush," has too much body stiffness, i.e., insufficient body length, it will not move out of the supply bin at normal operating pressure, and it will impart to the finished ink too much viscosity and surface tension.

Commercially flush is stored in large bins. To remove the flush, the bins are placed in apparatus equipped with a large hydraulic ram that presses the flush out of a square opening in the bottom of the bin. If the flush has insufficient flowability, it will not flow from the bin or it will flow very slowly. The measuring of the flow characteristics of a flush before it is removed from the storage bin is extremely important in order to maintain proper flow of the flush from the bin and in order not to increase production time.

In order to be controlled, the body stiffness and flowability must be measured and adjusted during manufacture. One conventional way of testing the flushed pigment is to determine the speed at which a mound of the material will spread out and to compare this with a standard, that is, a material that has been formulated to possess all of the required properties, e.g., strength, shade, tack, and flow, and that has been agreed by both the vendor and the customer to possess all of these properties within a specified range.

This procedure is not satisfactory because subtle variations in flow are not readily apparent nor can they be quantified.

Other means of measuring flowability also are not satisfactory. For example, the Ferranti Shirley instrument imparts to the flush a rotary shear; the readings obtained do not reflect or predict flowability.

The Laray Viscometer squeezes the flush between a steel rod and a cylinder; weights are put on top of the rods. The greater the weight, the faster the rod moves through the flush and the cylinder. This procedure is repeated several times to develop a slope that shows viscosity, but this subjects the flush to an input of energy in a form that is different from the energy input of a supply bin.

BRIEF DESCRIPTION OF THE INVENTION

It has now been found that the flowability of a flush can be measured accurately and the results of the measurements can be correlated with the actual production practice when the flush is evacuated from a supply bin equipped with a hydraulic piston. The flush is pressed down in a cylinder, the distance that it moves in a specified time is measured, and the distance is compared with the distance traveled in the same time by a standard material.

DETAILED DESCRIPTION OF THE INVENTION

The FIGURE is a cross-sectional view of the apparatus of this invention. It comprises external temperature control means (not shown), a cylinder 11, a water jacket 12, a piston 13, a means for measuring the distance that the piston travels (not shown), a cut-off plate 14, a water jacket sleeve 15, two retaining plates 16 (one not shown), and a timer (not shown).

The temperature control device monitors the temperature of the water jacket 12; the temperature range is limited only by the temperatures of production usage.

The cylinder 11 is suitably a barrel with a square orifice in its base. The dimensions of the cross-sectional area of the cylinder and of the orifice are directly proportional to the dimensions of the production flush supply bin.

The water jacket 12 encircles the cylinder 11 via a sealed sleeve 15 in order to stabilize the temperature of the cylinder and the piston.

The piston 13 is matched to the cylinder. It has a screw top and is hollow so that incremental weight can be added.

This variable weight capability provides test flexibility with respect to the pressure applied to the flush in the cylinder. The proportional pressure of the piston will then match the pressure applied by the hydraulic unit of the supply bin.

The dial indicator is equipped with a spring-loaded shaft and measures the distance traversed by the piston; it is capable of measuring $1.0 \times 10^{-4}$ inch increments.

The cut-off plate 14 slides in a track in the bottom of the water jacket. The cylinder bottom rests on the cut-off plate so that when the cut-off plate is pulled on the track and exposes the orifice in the cylinder base, the piston can force flush through the orifice. At the end of the test period, the cut-off plate can be pushed in to stop the flow of flush.

The timer is a stopwatch accurate to 1/10 second.

Preferably, but not necessarily, the water jacket is steel; the cylinder, the jacket cylinder sleeve, the piston, and the cut-off plate are machined stainless steel.

The basic procedure for measuring and controlling the flow properties of a flush and correlating them with actual production practice is as follows:

1. loading a cylinder 11 with the material to be tested;
2. placing a piston 13 on top of the material in the cylinder;
3. pressing an indicator down onto the piston;
4. pulling out a cut-off plate 14 at the bottom of the cylinder to permit the material to exit and, at the same time,
5. starting a timer;
6. measuring the distance traversed by the piston in a given time; and 7. comparing the distance with the distance traversed by a known standard material.

In actual practice, the unit is leveled to insure that the piston will travel perpendicularly to the cylinder plane.

A water bath 12 is attached to the unit by means of clear flexible tubing and calibrated to control the temperature of the moderating temperature fluid, such as a 50:50 percent by volume of distilled water:commercial anti-freeze, e.g. ethylene glycol. The temperature range of the water bath and the jacketed instrument is about 15° C. to 35° C., the temperature at which the flush will be removed from the storage bin in commercial operation.

The temperature of the flush is stabilized by keeping the flush in a metal or plastic sample container which is stored in the open water bath prior to loading the cylinder.

The alignment and steady position of the cylinder are maintained by two retaining plates 16.

The internal walls and bottom of the cylinder and the piston are wiped with gauze saturated with flush grease, such as for example a petrolatum-cup grease-orange solid oil, which (a) allows the instrument to measure the flow of the flush, not the resistance of the flush to flow against the bare metal of the cylinder, and (b) the thin coating of grease expedites the cleaning of the cylinder and the piston. The amount of grease used in the minimum that will lubricate without contamination.

The cylinder is loaded to about 75 percent of capacity with the flush. The piston is placed in the cylinder and a small amount of flush is pressed out to insure the absence of voids. The dial indicator is then pressed down onto the piston, compressing the spring-loaded shaft of the indicator. The compression should be at least 0.75 inch and can be as much as 1.000 inch. The cut-off plate must be completely in to prevent seepage of the flush from the orifice in the cylinder base.

The cut-off plate is then pulled out sufficiently to allow the flush to exit; at the same time the timer is started. The flow rate of the flush is noted on the dial indicator. In general, readings are taken after 5 minutes, 10 minutes, and 20 minutes.

The equipment is then cleaned and prepared for the next test by moving away the dial indicator; removing the cylinder, piston, and cut-off plate; squeezing out any residual flush; and removing all flush and grease from the instrument.

The data are interpreted as follows: the greater the distance traversed by the piston in a given time, the greater the flow of the flush; for example, if the distance traversed by the piston on the flush being tested is less than the distance traversed by the standard, the flush being tested has less flowability than does the standard.

The following data illustrate the results obtained by the instrument of this invention:

| Sample | Distance Traversed, inch | Time, minutes |
| --- | --- | --- |
| 1 | 0.0992 | 10 |
| 2 | 0.0544 | 10 |

Thus, because sample 1 traveled further in the same time than did sample 2, it has greater flowability.

The apparatus and process described herein directly simulate the equipment used in actual production and give accurate flowability data without extensive mathematical manipulation or interpretation.

Although the present invention is illustrated by measuring the viscosity of flushed pigments, the instrument can be utilized to measure the flow characteristics of any suitable material that is not a powder.

What is claimed is:
1. A process for measuring the flow properties of a non-powdered material and correlating them with actual production practice which comprises the steps of
    (1) loading the material to be tested into a cylinder, the cylinder having an orifice in its base and a cut-off plate which stops the flow of the material through the orifice;
    (2) placing a piston on top of the material in the cylinder, the piston weighing a known amount;
    (3) pressing an indicator down onto the piston;
    (4) pulling out the cut-off plate to permit the material to exit the cylinder and, at the same time,
    (5) starting a timer;
    (6) measuring the distance traversed by the piston in a given time; and
    (7) comparing the distance with the distance traversed by a known standard material.
2. The process of claim 1 wherein in step (1) the cylinder is loaded to about 75 percent of capacity.
3. The process of claim 1 wherein the material is loaded into the cylinder from a supply bin equipped with a hydraulic piston.
4. The process of claim 3 wherein the temperature of the material being tested is maintained in the cylinder at the temperature at which it had been in the supply bin of claim 3.
5. The process of claim 1 wherein the material being tested is a flushed pigment.
6. Process of claim 5 wherein the dimensions of the cylinder and of the orifice are directly proportional to the dimensions of a flush supply bin.
7. Process of claim 6 wherein the orifice is a square orifice.
8. Process of claim 1 wherein the piston and the cylinder are greased.
9. Apparatus for measuring the flow properties of a non-powdered material which comprises a cylinder having an orifice in its base and encircled by a water jacket via a sealed sleeve, a piston weighing a known amount inside the cylinder, a cut-off plate that slides in a track in the bottom of the cylinder to stop and permit the flow of the material, retaining plates to align the cylinder and hold it steady, a timer, means for controlling the temperature of material in the cylinder, and means for measuring the distance that the piston traverses.
10. The apparatus of claim 9 wherein the means for measuring the distance that the piston traverses is a dial indicator equipped with a spring-loaded shaft.
11. The apparatus of claim 9 wherein the material being tested is a flushed pigment.
12. Apparatus of claim 11 wherein the dimensions of the cylinder and of the orifice are directly proportional to the dimensions of a flush supply bin.
13. Apparatus of claim 12 wherein the orifice is a square orifice.
14. Apparatus of claim 9 wherein the piston and the cylinder are greased.

* * * * *